United States Patent
Beri

(10) Patent No.: US 9,439,723 B2
(45) Date of Patent: Sep. 13, 2016

(54) VARIABLE STIFFNESS CATHETER

(71) Applicant: Abhimanyu Beri, Redlands, CA (US)

(72) Inventor: Abhimanyu Beri, Redlands, CA (US)

(*) Notice: Subject to any disclaimer, the term of this patent is extended or adjusted under 35 U.S.C. 154(b) by 613 days.

(21) Appl. No.: 13/923,118

(22) Filed: Jun. 20, 2013

(65) Prior Publication Data

US 2014/0378945 A1 Dec. 25, 2014

(51) Int. Cl.
*A61B 18/14* (2006.01)
*A61M 25/00* (2006.01)
*A61M 25/01* (2006.01)
*A61B 18/00* (2006.01)

(52) U.S. Cl.
CPC ...... *A61B 18/1492* (2013.01); *A61M 25/0043* (2013.01); *A61M 25/0102* (2013.01); *A61B 2018/00577* (2013.01); *A61B 2018/00839* (2013.01); *A61M 2025/0064* (2013.01)

(58) Field of Classification Search
CPC .......... A61B 18/1492; A61B 2018/00577; A61B 2018/00839; A61M 25/0043; A61M 25/0102; A61M 2025/0064
USPC ............................ 604/95.05, 530, 531
See application file for complete search history.

(56) References Cited

U.S. PATENT DOCUMENTS

| | | | |
|---|---|---|---|
| 5,897,536 A | 4/1999 | Nap | |
| 5,957,966 A * | 9/1999 | Schroeppel et al. | A61N 1/056 607/119 |
| 6,146,381 A * | 11/2000 | Bowe et al. | A61M 25/0041 600/374 |
| 6,830,568 B1 * | 12/2004 | Kesten et al. | A61B 18/24 604/95.05 |
| 7,559,916 B2 | 7/2009 | Smith | |
| 7,645,275 B2 | 1/2010 | O'Connor | |
| 8,007,462 B2 | 8/2011 | Gibson | |
| 8,231,613 B2 | 7/2012 | Baxter | |
| 8,376,960 B2 | 2/2013 | Olson | |
| 2002/0082556 A1 | 6/2002 | Cioanta | |
| 2004/0230188 A1 | 11/2004 | Cioanta | |
| 2005/0027244 A1 * | 2/2005 | Eidenschink | A61M 25/0054 604/95.05 |
| 2010/0114270 A1 | 5/2010 | O'Connor | |
| 2011/0054393 A1 * | 3/2011 | Griffin | A61M 25/005 604/95.05 |
| 2013/0060310 A1 | 3/2013 | Saab | |

FOREIGN PATENT DOCUMENTS

| | | |
|---|---|---|
| WO | US93/10465 A1 | 5/1994 |
| WO | US2005/034487 A2 | 4/2006 |
| WO | US2009/049293 A1 | 1/2010 |

* cited by examiner

*Primary Examiner* — Manuel Mendez
(74) *Attorney, Agent, or Firm* — Trojan Law Offices

(57) ABSTRACT

A device and method for inserting a variable stiffness catheter into a subject with a catheter body being in relatively stiff state at a first temperature and a more flexible state at a second temperature. A temperature sensitive polymer is incorporated into the catheter that varies in stiffness depending on the temperature. The stiffness of the catheter is regulated by being in thermal contact with a circulating fluid within the catheter, or by being connected to resistive members in thermal contact with temperature sensitive alloys or polymers. The variable stiffness catheter can therefore be guided through the vasculature while in a relatively flexible state, but be changed into a relative stiff state during ablation procedures.

15 Claims, 5 Drawing Sheets

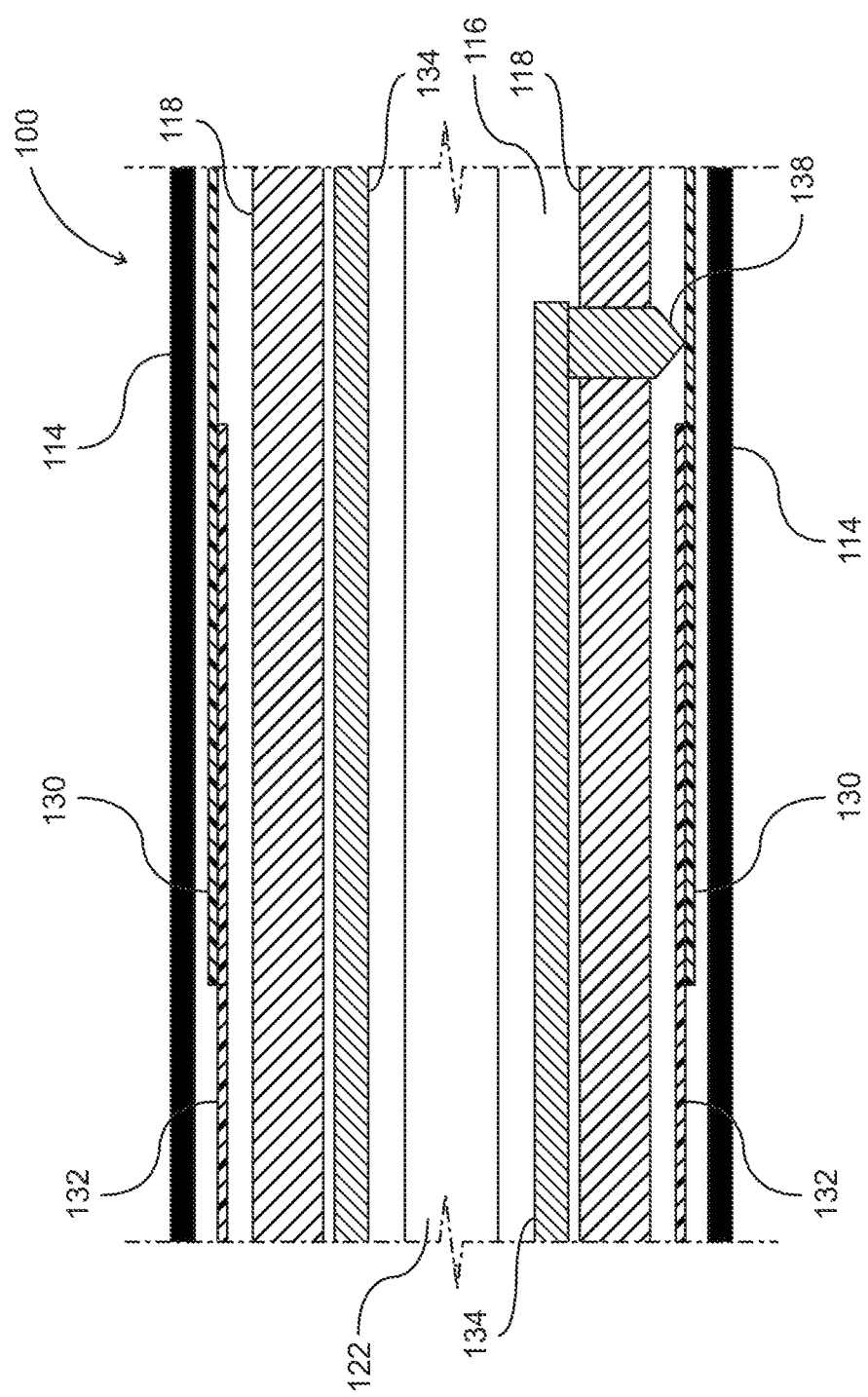

VARIABLE STIFFNESS CATHETER

FIELD OF THE INVENTION

This invention is directed to a medical device and methods of using a medical device. More specifically, this invention relates to catheters that vary in stiffness by using temperature sensitive polymers and alloys.

BACKGROUND OF THE INVENTION

Catheters are used to access treatment sites within the body by guiding the catheter through body cavities, ducts or vessels to the target site. Catheters have several uses in medicine and surgery and may be used to increase the diameter of a narrowed vessel (such as by using a balloon catheter to expand blood vessels), open Chronic Total Occlusions (CTO) in vessels, or ablate tissues using a high-energy source. The advantage to using a catheter for patient treatment is that the catheter allows the practitioner to target regions within the body by using minimally invasive techniques. To first reach the target location, a practitioner places the catheter through a small opening of a patient (such as a blood vessel) and guides the tip of the catheter through the vasculature until the tip reaches the desired target location within the body. Once the tip of the catheter is at the target site, the practitioner can use a variety of techniques to deliver treatment to the patient via the catheter tip.

Several conditions and diseases can be treated using catheters. For example, several heart rhythm disorders can be treated by using catheters that emit high-energy waves, or contain tissue freezing cryogenic fluid, at the tip of the catheter to ablate cardiac tissue causing the aberrant condition. Aberrant conditions include cardiac arrhythmias, such as Atrioventricular nodal reentrant tachycardia (AVNRT), Atrioventricular Reciprocating Tachycardia (AVRT), atrial fibrillation, atrial flutter, and ventricular tachycardia, to name a few.

Safe, effective catheters that are used to treat atrial fibrillation are highly desired because millions of people worldwide have are afflicted with this condition. Although ablation procedures using a catheter have great potential, however, the long-term success rate for ablation has not risen above at 50-60%. This long-term success rate has been partly attributed to the inability to permanently isolate the pulmonary veins. This inability to isolate pulmonary veins, and other target regions, are one of the many problems faced by practitioners using present-day catheters. The inability to effective target treatment locations is often due to the lack of stability of the catheter (i.e., the inadvertent movement of the catheter during use). The lack of stability is partly due to the required flexibility of the catheter to reach the target site.

An ideal catheter must be flexible enough to be steered within the vasculature of the patient, however, if too flexible, the catheter will likely buckle and not advance properly. The stiffer the catheter, the more stable the position, however, a stiff catheter has several other problems. First, if it is too stiff, the catheter will not be able to make the tortuous turns in the vasculature to reach the treatment site, and second, a stiff catheter is more likely to damage delicate tissues within the patient.

Specifically for the treatment of a rhythm disorder, catheters are first introduced into the body via a vein or artery and then guided under fluoroscopic or magnetic guidance to relevant regions of the heart to diagnose the cause of this abnormal rhythm. To treat this abnormal rhythm, one technique is to ablate the responsible tissue in the heart. When the tissue is ablated, the correct heart rhythm is hopefully restored. To ablate the cardiac tissue, the practitioner uses a catheter having a deflectable tip that the practitioner is able to direct by using tension wires within the catheter to aim the tip toward the target tissue. When the tip is at the desired location, the practitioner uses the catheter to deliver energy, which ablates the tissue. The technique of energy delivery includes but is not limited to radiofrequency, cryogenic tissue freezing tissue and laser beams.

While in theory the tip of the catheter that emits high energy is pointed only at the tissue that should be ablated, the catheter may move during any number of steps of the procedure. For example, the catheter may move while the practitioner obtains intra-cardiac electrogram, cardiac pacing, or during ablation itself. Repositioning the catheter can be both time consuming, frustrating, and prevent successful ablation. It can also potentially cause complications if the catheter moves during ablation because if the catheter moves during ablation, the wrong cardiac tissue may be ablated and damage the normal conduction pathways needed for proper heart functioning or even cause structural damage including perforation of the heart tissue.

There have been several attempts to increase stability of the catheter. One way to increase stability is the use of long, deflectable sheaths. However, these sheaths can be cumbersome, with higher potential of thrombosis within sheathes. Another way to increase stability is the use of remote navigation systems. However, remote navigation systems have high initial startup as well as ongoing costs and are cumbersome to use, thereby preventing widespread adoption.

Therefore, it would be beneficial to provide a catheter that has sufficient flexibility to be easily manipulated, be stiff enough to maintain its shape once a target location is reached, not require sheath exchange, have inexpensive startup and operation costs, and be usable with currently available and installed technologies.

SUMMARY OF THE INVENTION

The present invention relates to a catheter made of materials that have properties that can change in response to temperature. Specifically, embodiments of the invention use materials that affect the stiffness of the catheter. The variable stiffness is enabled by the use of temperature sensitive polymers incorporated into sleeves, tubes and/or cords within the catheter. The stiffness and flexibility of these sleeves, tubes and/or cords depending on the temperature of the polymer. The temperature sensitive polymers are in thermal contact with a heating and/or cooling source within the catheter. The catheter stiffness is controlled by the practitioner by controlling the temperature within the catheter. By using temperature controls, the practitioner can keep the catheter in a flexible state when the catheter needs to be guided through the patient, but can be changed into a stiff state when the catheter reaches the treatment location.

The temperature, and thus stiffness, of the catheter can be changed using a variety of methods and catheter embodiments. In one embodiment, the catheter can be in a relatively flexible state when the catheter is at the normal body temperature of 98.6° F. (37° C.). The temperature of the catheter can be changed by circulating a fluid within the catheter having a specific temperature that allows the catheter to be in either more flexible state or more stiff state. When the temperature of the circulating fluid thermally contacts the temperature sensitive polymer incorporated into the sleeves, tubes, and/or cords of the catheter, the stiffness of the catheter changes. There are several advantages of the variable stiffness catheter. When the catheter is in a flexible state when it is being guided through the vasculature, it reduces the chance of puncture because the catheter can bend with the curvature of the vasculature. Stiffening the catheter when the catheter tip reaches the target location allows the practitioner to safely target a treatment area, since a stiff catheter is less likely to unintentionally move or jump to a non-targeted region. Furthermore, the use of circulating fluid to change the temperature of the catheter is relatively inexpensive. Therefore this type of temperature fluid controlled catheter has both the advantages of a flexible catheter and stiff catheter, while remaining inexpensive and easy to use. The process of stiffening the catheter for treatment by changing the temperature of the fluid is also advantageous because it is repeatable and reversible.

In one embodiment, the catheter has a body having proximal portion, a distal portion, and a distal tip at one end of the distal portion. Forming the outer exterior surface is a flexible outer cylindrical tubing. The inside of the tubing forms an inner catheter body lumen. Within the inner catheter body lumen is an elongated supporting core situated along the central lengthwise axis of the catheter shaft. Within the shaft lumen are several elements used for temperature transfer, which control the stiffness of the catheter.

One way to control the temperature of the lumen is the use of an elongated inner tubing capable of receiving and circulating a fluid (with the tubing located inside of the body of the catheter). The inner tubing can circulate fluid of different temperatures, and the practitioner can control temperature and flow of the fluid within the catheter. Therefore, the practitioner has the ability to affect the stiffness of the catheter without affecting the shape of the catheter at that time (that is, stiffness and shape are independently controlled by the practitioner and the catheter can be stiffened while maintaining a desired curvature). At least one member of the catheter is made from a material having a temperature sensitive polymer. In one embodiment, the polymer has a first stiffness at a first temperature and a second stiffness (different from the first stiffness) at a second temperature. In a preferred embodiment, the stiffness of the catheter progressively becomes stiffer in response to the increase or decrease in the temperature of the temperature sensitive polymer, that is stiffness of the catheter ideally is a continuous variable instead of a discrete variable which is correlated a temperatures between the first temperature and the second temperature that the operator controls. When the fluid transfers its heat energy to or away from the portions of the catheter having the temperature sensitive polymer, the stiffness of those materials having the temperature sensitive polymer changes, thereby affected the stiffness of the catheter as a whole.

In one embodiment, only some regions or portions of the catheter shaft are made from temperature sensitive polymers. In another embodiment, the flexible outer cylindrical tubing forming the exterior surface of the catheter body is made from a temperature sensitive polymer. In yet another embodiment, the elongated inner tubing is made from a temperature sensitive polymer. In yet another embodiment, sleeves that are underneath the flexible outer tubing are made from the temperature sensitive polymer. In still yet another embodiment, a combination of more than one member of the catheter is made from temperature sensitive polymers.

In other embodiments, temperature sensitive polymer cords are placed within the lumen of the body, and in thermal contact with the fluid passed through the catheter. In one embodiment the fluid is circulated in a closed loop system, where the heated or cooled fluid is retrieved within the catheter to allow for continuous operation without flowing into the body. In other embodiments, the fluid may be in an open tubing system, where the heated or cooled fluid is not retrieved and enters the body after circulation within the catheter.

In other embodiments, a vascular sheath may be used to insert the catheter into the body. The sheath may be partly or completely made of temperature sensitive polymers whose stiffness can be varied based on temperature. Thus, the stiffness of the sheath can be adjusted based on the temperature of the fluid circulated or flushed through the sheath. Such a sheath can also be used to deliver other diagnostic and therapeutic devices inside the body, including, but not limited to: ablation catheters, stents, coils, wires, ultrasound probes, valves, and closure devices.

In other embodiments, the catheter can have a first region with a first temperature sensitive polymer, and a second region having a second temperature sensitive polymer, the two temperature sensitive polymers having different temperature sensitive characteristics. This type of embodiment has the advantage of a single catheter having different stiffness in different regions, all while circulating fluid having a single temperature.

While elongated tubing within the catheter shaft for circulating fluid is one way to change the temperature of the temperature sensitive polymers, other embodiments may use a different means to change the temperature of the temperature sensitive polymers, thereby changing the stiffness of the catheter. In one embodiment, wires within the catheter shaft extend through the shaft and connect to resistive members in contact with at least one member having a temperature sensitive polymer. The practitioner controls the current and voltage, extending from a power supply connected to resistive members within the catheter shaft. As current is passed through to the resistive members, the resistive members increase in temperature, and transfer the heat to the temperature sensitive polymers. In one embodiment, the heat is transferred to temperature sensitive polymer sleeves that change the sleeves from a stiffer state to more flexible state. Other embodiments may use thermoplastics that are stiffer when heated, and more flexible when cooled.

In yet another embodiment of a variable stiffness catheter, the catheter has a temperature sensitive metal alloy (also known as a shape memory alloy (SMA)), that retains (i.e. remembers) the shape it was in at a previous temperature. The alloy can be deformed and change shape when guided though the vasculature, but returns to its pre-deformed state when the practitioner applies a specific temperature to the alloy. The shape memory alloy also is responsive to changes in temperature to selectively change the stiffness, as well as the shape, along the catheter. In this embodiment, the practitioner can use a preset dormant shape and stiffness for use when guiding through the vasculature, then change the temperature (and thus the shape of the catheter) when the tip of the catheter is at the target region.

The embodiments described above may have additional features such power supplies, handles, knobs for deflecting a tip, and controls for circulating fluid and/or electrical conduction known in the art. These features and others may be incorporated into a handle portion or other externally located region of the catheter device or apparatus, located at the proximal end of the catheter body. The handle portion may have a steering mechanism allows the practitioner to deflect the tip of the catheter to a desired location or angle, to target a specific region for ablation. In one embodiment, the steering mechanism would use tension wires running through the length of the catheter and connect to the handle. In a preferred embodiment, the handle is connected to an external energy generator to enable delivery of high energy RF waves or other forms of energy to ablate appropriate tissue.

In another embodiment, a method of targeting a treatment location within the human body is disclosed. The practitioner inserts the temperature sensitive catheter using any one of the embodiments above. The practitioner then circulates a fluid having an initial temperature in the inner tubing to keep the catheter in a relatively flexible state while guiding the catheter through the vasculature to the desired target site. The practitioner then circulates fluid having a cooler temperature through the inner tubing to stiffen the catheter. Once the catheter is in a relatively stiff state, the practitioner delivers the treatment to the treatment location via the distal tip of the catheter (such as RF energy, cyroenergy, or other treatments that ablate tissue or target tissue using medication).

In another embodiment of a method of targeting a treatment location, instead of changing the temperature of a fluid within the catheter, the practitioner changes the current in wires (connected resistive members which increase in temperature when a current is applied) within the catheter, in order change the temperature of the temperature sensitive polymers, thereby changing the flexibility of the catheter.

The example embodiments above have been used to describe the problem and embodiments of the present invention, but it can be appreciated that this same concept can be used in any part of the body. These and other aspects and advantages of the invention will become apparent form the following detailed description and the accompanying drawings, which illustrate by way of example the features of the invention.

BRIEF DESCRIPTION OF THE DRAWINGS

FIG. 5 is a long axis cross-sectional view of the embodiment of FIG. 4.

DETAILED DESCRIPTION OF THE INVENTION

Figure 1:
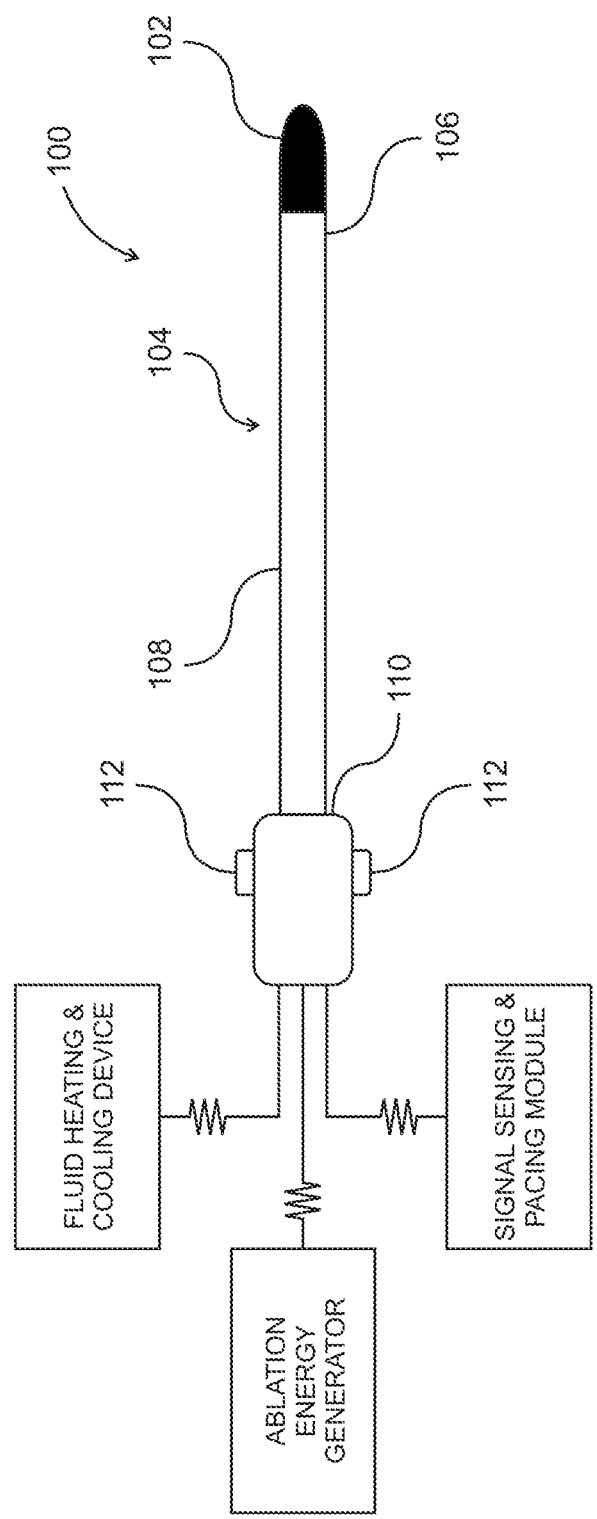
FIG. 1 is a side view of a catheter having a control handle and ablation energy delivery tip.

The invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

It will be understood that when an element is referred to as being "on" another element, it can be directly on the other element or intervening elements may be present there between. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section.

The terminology used herein is for the purpose of describing particular embodiments only and is not intended to be limiting of the invention. As used herein, the singular forms "a," "an," and "the," are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another elements as illustrated in the Figures. It will be understood that relative terms are intended to encompass different orientations of the device in addition to the orientation depicted in the Figures.

Unless otherwise defined, all terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments of the present invention are described herein with reference to idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes that result, for example, from manufacturing.

FIG. 1 is a side view of an embodiment of an overall design of a variable stiffness catheter 100 for use within the vasculature of the human body. The catheter 100 has a shaft or body 104, which comprises a distal region 106, a proximal region 108 and a distal tip 102 extending from the distal region 106. The distal tip 102 targets a treatment site within a patient by emitting high energy radio frequency (RF) waves to ablate tissues and is an ablation member. In other embodiments, the tip 102 may deliver medications or cryogenic fluid to target regions. High energy RF waves destroy tissues causing abnormal electrical pathways leading to cardiac arrhythmias. For cardiac ablation treatments the tip 102 is placed within the heart, usually through a vein, and guided to the tissue the practitioner wants to ablate. Cryoablation, microwave ablation, ultrasound ablation, or laser ablation of tissue may be accomplished with different types of tips, catheters, and energy sources.

The tip 102 of the catheter can be controlled by the practitioner, who maneuvers the catheter 100 using a catheter handle 110. The handle 110 has deflection knobs 112 that can control the deflection of the tip 102 so that the practitioner can angle (i.e. deflect) the tip 102 in a variety of directions so that the catheter 100 can be easily guided through the vasculature, as well as aiming the tip 102 directly at the tissue the practitioner wants to ablate. The catheter 100 is connected to an ablation energy generator (power sources), a fluid heating and cooling device, and a signal sensing and pacing module. The ablation energy generator controls the RF energy that emits from the tip 102. The signal sensing and pacing module detects and determines heart arrhythmias and the fluid heating and cooling device allows for fluid to be circulated within the catheter body 104. The practitioner controls the temperature of the catheter body 104 by using the heating fluid/cooling device. Other modules connected to the body 104 of the catheter 110 may replace the modules and generators of FIG. 1 for other types of ablation techniques, such as for cryoablation, microwave ablation, laser ablation, or any other type of ablation.

Figure 2:
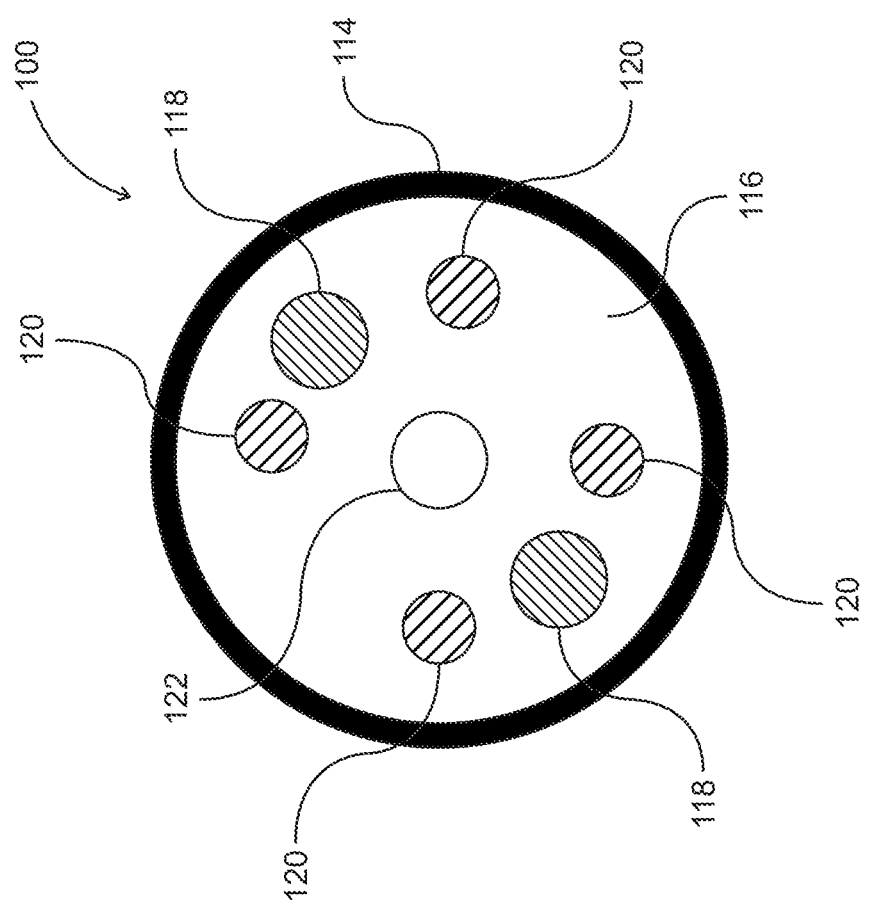
FIG. 2 is a short axis cross-sectional view of a conventional catheter having deflecting wires, a supporting core, and insulated sensing, pacing, and energy deliver wires.

The elongated catheter body 104 can house many members that help the practitioner safely guide the catheter 100 through the patient to the target region. FIG. 2 is a short axis cross-sectional view of a conventional catheter not having any temperature sensitive members. The catheter 100 has an outer polymer shell 114 which is a substantially cylindrical tubing that forms the exterior surface of the catheter shaft 104. The cylindrical tubing 114 forms an inner shaft lumen 116, which can house several of these members. For example, the inner lumen 116 may house deflecting wires 118 that allow the operator to maneuver and point the distal tip 102. When the knobs 112 are depressed by the practitioner, the knobs control the tension in the deflecting wires 118, which thereby deflect the tip 102 in different directions, depending on which knobs 112 and how much the knobs 112 are depressed. In addition, electric wires 120 are also disposed within the lumen 116 and extend from the proximal end of the catheter body 108 to the tip 102. These wires are electrically connected to the signal sensing and pacing module and/or ablation energy generator (as depicted in FIG. 1). Extending substantially through the elongated axis of shaft 100 is a supporting core 122, which may be hollow or solid, and supports the catheter structure. As one can see from the embodiment of FIG. 2 that there are no means to allow the catheter 100 to have variable stiffness. This catheter 100 will remain in the same relatively flexible or relatively stiff state through the procedure.

Figure 3:
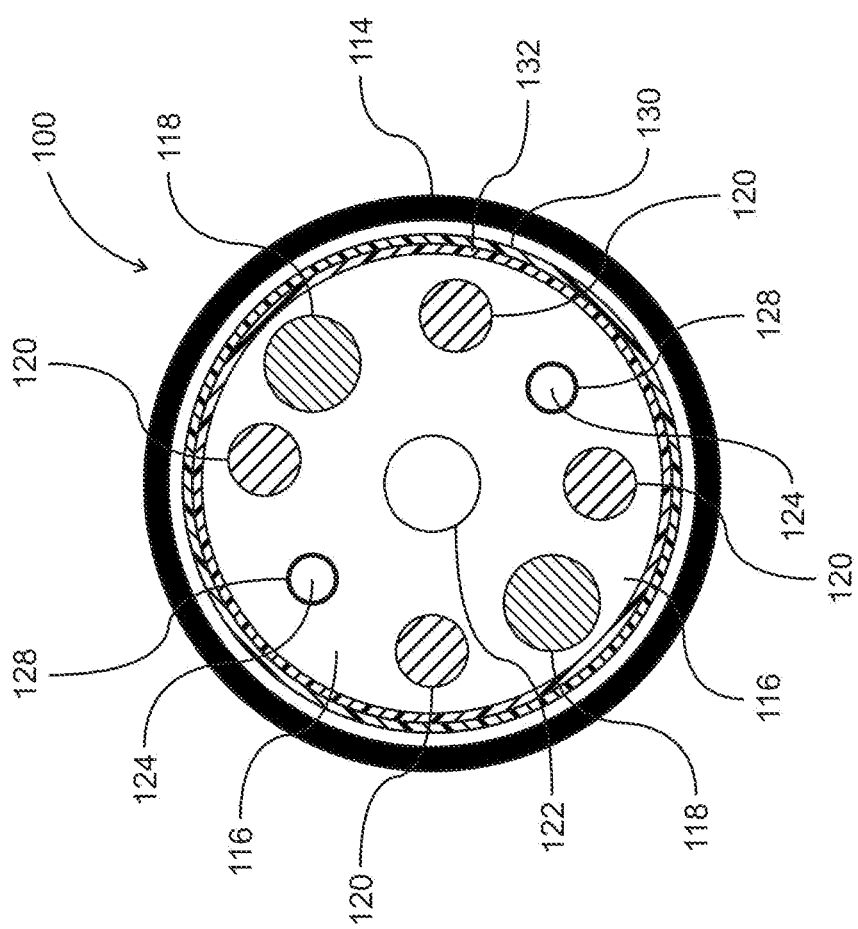
FIG. 3 is a short axis cross sectional view of an embodiment of a temperature regulated variable stiffness catheter with fluid circulating tubes and overlapping temperature sensitive polymer sleeves.

In contrast to the catheter of FIG. 2, which has no means for the operator to control the stiffness, FIG. 3 depicts an embodiment of the present invention that can vary in stiffness. FIG. 3 illustrates the short axis cross-sectional view of a temperature regulated variable stiffness catheter 100. Besides the conventional members found in commonly used catheters not having any temperature control (as depicted in FIG. 2), the variable stiffness catheter 100 has additional temperature sensitive members and temperature controls. Concentric with the outer cylindrical tubing 114 are a first temperature sensitive sleeve 130 and a second temperature sensitive sleeve 132. In cross-section as shown in FIG. 3, these sleeves overlap, and in FIG. 5, an embodiment of the overlapping sleeves 130, 132 is better illustrating as showing the overlapping and non-overlapping portions of the sleeves 130, 132. The sleeves 130, 132 are comprised of a composition having a temperature sensitive polymer. The temperature sensitive polymer varies in stiffness depending on its temperature. Within the catheter body lumen 116 is an inner tubing 128 which has an inner tubing lumen 124 where fluid of various temperatures can circulate the catheter 100. Although not necessarily physically contacting the sleeves 130, 132, the tubing 128 allows for thermal contact of the sleeves 130, 132, permitting heat to transmit between the fluid in the lumen 124 of the inner tubing 128 to the sleeves 130, 132. The sleeves 130, 132 can therefore be warmed or cooled by the circulating fluid controlled by the practitioner. When the catheter is being cooled by fluid to stiffen the catheter, heat transfer will be from the sleeves 130, 132 (or other member comprised of the temperature sensitive polymer) to the circulating fluid.

In an embodiment depicting the inner tubing 128, the tubing is connected to the fluid heating and cooling device (as depicted in FIG. 1) and operated by the practitioner who controls the flow and temperature of the circulating fluid. In some embodiments, more than one inner tubing may circulate the fluid, and the inner tubing may be in a closed loop or open loop configuration. In some embodiments, the sleeves 130, 132 may be made from the same composition having temperature sensitive polymers, while in other embodiments, the sleeves 130, 132 may be made from different temperature sensitive polymers, such that the stiffness of the first sleeve 130 may be different than the stiffness of the second sleeve 132, such that the sleeves will vary in flexibility with respect to each other, even when at the same temperature.

The sleeves 130, 132 may run the entire length of the catheter body 104, or may run only partially with the catheter body 104. As the sleeves 130, 132 approach the distal portion 106 of the catheter body 104, movement of the tip 102 will be reduced when the sleeves 130, 132 are in a stiff state. When movement of the tip 102 is reduced, and targeted to tissue for ablation, there is less chance that the catheter tip will move or jump during the ablation process, and thus the ablation procedure is safer with a stiffened distal region 106. While the use of sleeves 130, 132 is means to have variable flexibility in FIG. 3, temperature sensitive polymers can be incorporated into the outer cylindrical tubing 114, the inner tubing 128 for circulating fluid, temperature sensitive cords (not illustrated), or the supporting core 122.

Figure 4:
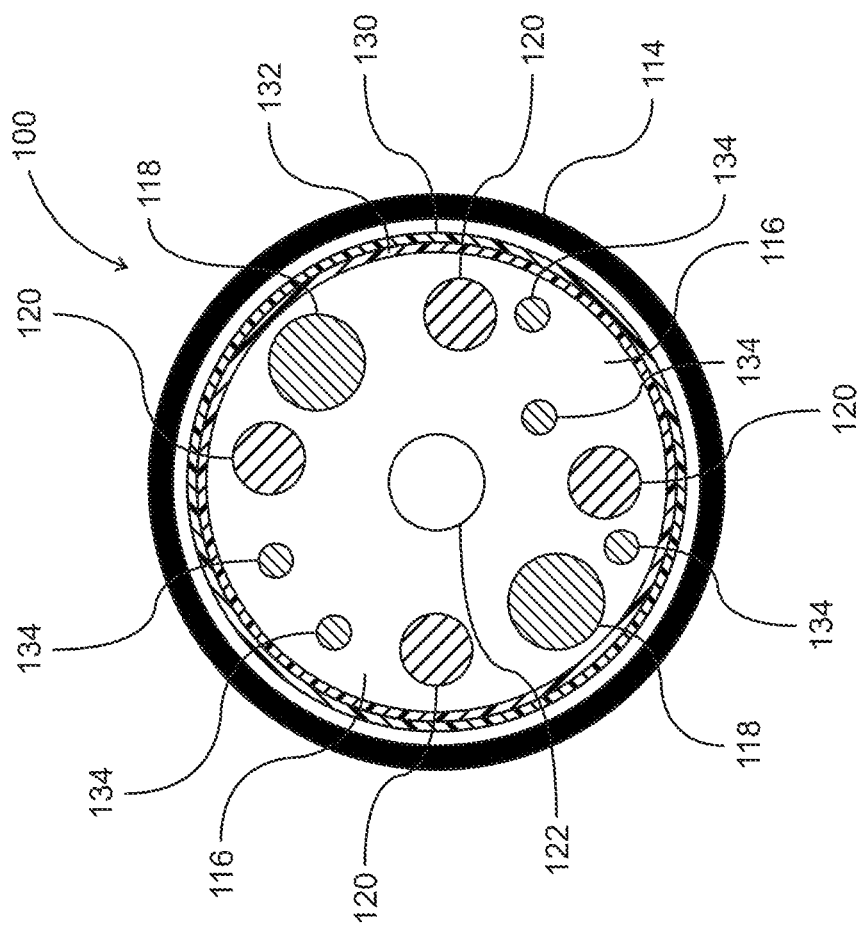
FIG. 4 is a short axis cross-sectional view of an embodiment of an electrically controlled temperature regulated variable stiffness catheter and overlapping temperature sensitive polymer sleeves.

In another embodiment of the invention, as depicted in FIG. 4 and FIG. 5, instead of using an inner tubing 128 to circulate a fluid within inner tubing lumen 124 (as depicted in FIG. 3), heat is transferred via electrical wires 134 coated with a temperature sensitive polymer. The wires 134 are electrically connected to a resistive member 138 (such as a resistive strip) which increases in temperature when a current is applied via the wires 134. FIG. 4 depicts the short axis cross section of such a catheter 100 having overlapping sleeves 130, 132, and resistive elements 138, FIG. 5 depicts the long axis of the catheter 100 in cross-sectional view. The wires 134 connect to a module that can control the heating or cooling of the wires 134 by varying current. Different wires 134 connected to different sleeves 130, 132 can stiffen or relax individual sleeves 130, 132 to stiffen or relax portions of the catheter 100 independently. The process of heating and cooling, stiffening and making more flexible, is both reversible and repeatable.

Temperature sensitive polymers for use in the embodiments of the invention described above included those commonly known in the art, such as: polymethyl methacrylate (PMMA), polyamides such as nylon, polypropylenes, polystyrenes, polyvinyl chlorides, and polytetrafluoroethylene (PTFE). Shape memory polymers are a subgroup of thermoplastics that retains a preformed shape at a given temperature. Such shape memory polymers include polyurethanes, polyethylene terephthalate (PET), polyethyleneoxide (PEO), polystyrenes, polybutadiens, polytetrahydrofurans, polynorbonene, oligosilsesquioxane, pyrolidone compounds, polyether ketones, crystalline diene polymers, PEO-PET polymers, or any other shape memory and/or temperature sensitive polymer known in the art.

Such shape memory polymer may be comprised of covalent and non-covalent bonds where the shape memory polymer can "remember" a shape upon an application of stimulus, such as heat. Cross-linking of molecules within the polymer facilitates return to the original or preset shape of the polymer. The memory polymer may transition from a programmed temporary shape into the permanent shape following a temperature increase or decrease. The shape memory polymer may remain in a deformed position at a temperature higher than a transition point and lower than the molding temperature of the memory shape polymer. The shape memory polymers remain in a deformed state that recover their original molded shape when heated to a temperature higher than a predetermined temperature and lower than the molding temperature. That is, the shape memory polymer takes on the as-molded shape and the deformed shape as the temperature changes.

Shape memory alloys are like temperature sensitive polymers, but are combinations of various metals that retain a preset shape when the polymer is subjected to a specific temperature and returns from its deformed shape to its preset shape when the allow reaches a threshold temperature.

Thus, shape memory alloys are advantageous for use in catheters because the catheter can be configured to be in a specific shape at one temperature, but be able to be molded and flex when at different temperature. The practitioner can apply the heat necessary to the catheter to transition the catheter into a preset shape once the catheter is in the desired location for treatment. Various shape memory alloys are known in the art and include alloys made from copper-aluminum-nickel, nickel-titanium, zinc, copper, gold or iron. Common nickel-titanium alloys (such as those commercialized under the trade name Nitinol) are commonly known in the art and change from austenite to martensite upon cooling, allowing the alloy to maintain a deformed shape below a threshold temperature and revert to a preset shape above a threshold temperature.

A number of references provide compositions for temperature sensitive/shape memory alloys and shape memory polymers, which are hereby incorporated by reference in their entirety herein: U.S. Pat. No. 7,628,116 entitled "Shape memory polymer temperature sensing devices and methods of use" to Browne et al., U.S. Pat. No. 8,124,691 entitled "Shape memory polymer with polyester and polyacrylate segments and process for its production" to Benin et al., U.S. Pat. No. 4,919,133 entitled "Catheter apparatus employing shape memory alloy structures" to Chiang, U.S. Pat. No. 8,365,833 entitled "Variable Tg shape memory polyurethane for wellbore devices" to Carey et al, U.S. Pat. No. 8,272,214 entitled "Shape memory alloy cables" to Aase et al., U.S. patent application Ser. No. 13/401,606 entitled "Functionally Graded Shape memory Polymer" to Mather et al., U.S. patent application Ser. No. 13/441,764 entitled "Implantation of shape memory polymer intraocular devices" to Kahook et al., U.S. patent application Ser. No. 13/175,396 entitled "Shape memory polymer containing composite materials" to Kia et al. The compositions of these temperature sensitive and shape memory polymers may therefore be incorporated into one, or more than one, member of the catheter to provide a temperature sensitive catheter.

While the sleeves 130, 132 of the catheter 100 can be relaxed by heating the wires 134 and sleeves 130, 132, the smart polymer sleeves 130, 132 can be stiffened by cooling fluid through the catheter to lower a temperature, or, depending on the type of shape memory alloy, may be stiffened by circulating warm fluid through the catheter 100. In a preferred embodiment, the polymer sleeves 130, 132 are stiffened by cooling fluid through a catheter to lower the temperature below 34 degrees Celsius. In other embodiments, the catheter may be stiffened or softened at a temperature at or above 40 degrees Celsius. In one embodiment, resistance 134 wires may be made from Nitinol or other smart metal alloy that can return to a preset shape when heated above a transformational temperature, but can be molded into a different shape below the transformational temperature. The above-mentioned embodiments will help with navigation of the catheter 100 and directing of the catheter 100 to a target location by, for example, stiffening the proximal 108 or distal end 106 of the catheter body. In some embodiments, the sleeves 130, 132 of the catheter 100 may fully encircle the inner circumference of the catheter shaft (as depicted in FIG. 3). In other embodiments, variable single sided/semi circular sleeves may also be used to provide secondary and tertiary curves to the catheter 100.

There are numerous applications for the use of the embodiments of the invention described above. One such application is ablating tissue on the cavo-tricuspid isthmus. Atrial flutter occurs with ridges on the isthmus that prevent prolonged stable contact. A catheter in a soft flexible state is likely to fall off either side of the ridge, but with a controllable stiffness catheter, the ablation tip of the catheter is more stable at a target position, and can safely deliver energy to a specific location.

Another application is for the treatment of AV nodal reentrant tachycardia (AVNRT). Ablation must occur close to the AV node, and any minor movement that would lead to ablation away from the AV note may be catastrophic. In still another application, atrial fibrillation may be treated using a pulmonary vein isolation (PVI) catheter application procedure.

While the invention has been described in terms of exemplary embodiments, it is to be understood that the words which have been used are words of description and not of limitation. As is understood by persons of ordinary skill in the art, a variety of modifications can be made without departing from the scope of the invention defined by the following claims, which should be given their fullest, fair scope.

I claim:
1. A variable stiffness catheter for use within the vasculature of the human body, the catheter comprising:
   a) a catheter body having a proximal portion, a distal portion, and a distal tip at one end of said distal portion;
   b) a flexible outer cylindrical tubing forming an exterior surface of said catheter body and an inner catheter body lumen;
   c) an elongated supporting core within said flexible outer cylindrical tubing, said supporting core situated along a central axis of said catheter body; and,
   d) an elongated inner tubing capable of receiving a circulating fluid within said inner catheter body lumen,
   e) a first temperature sensitive sleeve disposed within and substantially concentric with said outer cylindrical tubing;

f) a second temperature sensitive sleeve disposed within and substantially concentric with said outer cylindrical tubing, said second temperature sensitive sleeve at least partially overlapping said first temperature sensitive sleeve;

wherein said first and second temperature sensitive sleeves are each comprised of a temperature sensitive polymer;

wherein said first sleeve has a first stiffness at a first temperature and said second sleeve has a second stiffness at a first temperature, said second stiffness being different from said first stiffness, thereby allowing different regions of said catheter to have different stiffnesses at the same temperature;

wherein said elongated inner tubing is in thermal contact with said first and second temperature sensitive sleeves;

whereby a practitioner regulates the stiffness of said catheter by regulating the temperature of the circulating fluid, thereby allowing the practitioner to safely maneuver said catheter through the vasculature in a relatively flexible state, and apply treatment to a target position when said catheter is in a relatively stiff state.

2. The catheter of claim 1, wherein said distal tip comprises an ablation energy emitting member configured to ablate tissue.

3. The catheter of claim 1, further comprising an elongated temperature sensitive cord disposed within said inner catheter body lumen.

4. The catheter of claim 1, wherein said elongated inner tubing is configured in a closed loop formation.

5. The catheter of claim 1, wherein said elongated inner tubing is configured in an open loop formation.

6. The catheter of claim 1, wherein said temperature sensitive polymer is a thermoplastic shape memory polymer.

7. The catheter of claim 6, wherein said thermoplastic shape memory polymer comprises a material selected from the group of polyurethane polymers, styrene-butadiene polymers, crystalline diene polymers, norbanone polymers, polyethylene terephthalate, polyethyleneoxide, polystrene polytetrahydrofuran, polynorornene, and oligosilsequioxane.

8. The catheter of claim 1, wherein said temperature sensitive polymer softens at a temperature above human body temperature and stiffens at a temperature at or below 34 degrees Celsius.

9. The catheter of claim 1, wherein said temperature sensitive polymer substantially softens at a temperature at or above 40 degrees Celsius.

10. The catheter of claim 1, further comprising:
a handle connected to the proximal portion of said catheter body, said handle having steering mechanism for deflecting said distal tip;
a power supply for generating ablation energy, said power supply electrically connected to said catheter body;
an ablation energy controller electrically connected said power supply;
a first electrical conductor connecting ablation energy controller to said distal tip for regulating energy emitted from said distal tip;
a fluid controller for regulating fluid flow and fluid temperature, said fluid controller capable of regulating the flow rate and temperature of a fluid within said catheter body.

11. The catheter of claim 1, further comprising a sheath comprising a temperature sensitive shape memory alloy or polymer, said sheath capable of delivering diagnostic and/or therapeutic devices within a human body.

12. A variable stiffness catheter for use within the vasculature of the human body, the catheter comprising:
a) a catheter body having a proximal portion, a distal portion, and a distal tip at one end of said distal portion;
b) a flexible outer cylindrical tubing forming an exterior surface of said catheter body and an inner catheter body lumen;
c) an elongated supporting core within said flexible outer cylindrical tubing, said supporting core situated along a central axis of said catheter body; and,
d) a plurality of elongated overlapping temperature sensitive sleeves, said sleeves concentric with said flexible outer cylindrical tubing;
e) wherein said plurality of overlapping temperature sensitive sleeves comprises a first sleeve having a first stiffness at a first temperature and a second sleeve having a second stiffness at a first temperature, said second stiffness being different from said first stiffness, thereby allowing different regions of said catheter to have different stiffnesses at the same temperature.

13. The catheter of claim 12, further comprising:
a wire within said inner catheter body lumen, said wire electrically connected to a power supply;
an electrically resistive member electrically connected to said wire on a first end, and to at least one of said plurality of elongated overlapping temperature sleeves on a second end;
whereby said electrically resistive member is capable of transferring heat to said at least one of said plurality of elongated temperature sensitive sleeves when current is applied to said wire, thereby varying the stiffness said catheter.

14. The catheter of claim 12, wherein at least one member of said catheter comprises a shape memory alloy extending at least partially within said inner catheter body lumen, said at least one member returns to a pre-deformed shape when heated, thereby alloying a practitioner to maneuver said catheter in a flexible deformed shape at a first temperature, and deliver treatment while catheter is in a pre-deformed shape at a second temperature.

15. A method of targeting a treatment location within the human body, the method comprising:
a) inserting a temperature sensitive catheter having a first temperature within a patient, said catheter having an inner tubing capable of receiving a circulating fluid within said catheter body lumen and a distal tip, wherein said catheter has a first temperature sensitive sleeve and a second temperature sensitive sleeve overlapping said first temperature sensitive sleeve, wherein said first temperature sensitive sleeve has a first stiffness at a first temperature and said second temperature sensitive sleeve has a second stiffness at a first temperature, said second stiffness being different from said first stiffness, thereby allowing different regions of said catheter to have different stiffnesses at the same temperature;
b) circulating a fluid having a first temperature within said inner tubing such that said catheter is in a relatively flexible state;
c) guiding said catheter through the vasculature of said patient while said catheter is in a relatively flexible state until said distal tip reaches said treatment location;
d) circulating a fluid having a second temperature through said inner tubing, said second temperature being different than first second temperature, thereby changing said catheter from a relatively flexible state to a relatively stiff state;

e) delivering a treatment to said treatment location via said distal tip while said catheter is in a relatively stiff state.

* * * * *